United States Patent [19]

Gorsen

[11] Patent Number: 4,827,915
[45] Date of Patent: May 9, 1989

[54] SPRING LOADED CERVICAL COLLAR

[76] Inventor: Robert M. Gorsen, 1549 Bruton Ct., McLean, Va. 22102

[21] Appl. No.: 247,399

[22] Filed: Sep. 21, 1988

[51] Int. Cl.$^4$ .............................................. A61H 1/02
[52] U.S. Cl. .................................. 128/75; 128/87 B; 128/DIG. 23
[58] Field of Search ..................... 128/75, 76 R, 84 R, 128/87 B, DIG. 23

[56] References Cited

U.S. PATENT DOCUMENTS

| | | | |
|---|---|---|---|
| 2,474,200 | 6/1949 | McBee . | |
| 2,801,630 | 8/1957 | Moore . | |
| 2,807,260 | 9/1957 | Teufel . | |
| 2,820,455 | 1/1958 | Hall . | |
| 2,904,040 | 9/1959 | Hale | 128/DIG. 23 |
| 2,973,029 | 2/1961 | Schlosstein | 128/DIG. 23 |
| 3,027,894 | 4/1962 | Moore | 128/75 |
| 3,103,215 | 9/1963 | Schmidt | 128/75 |
| 3,364,926 | 1/1968 | Alderson | 128/75 |
| 3,601,123 | 8/1971 | McFarland | 128/DIG. 23 |
| 3,756,226 | 9/1973 | Calabrese et al. . | |
| 3,776,224 | 12/1973 | McFarland | 128/DIG. 23 |
| 3,916,885 | 11/1975 | Gaylord | 128/DIG. 23 |
| 4,582,051 | 4/1986 | Green et al. | 128/87 B |

Primary Examiner—Edgar S. Burr
Assistant Examiner—Huong Q. Pham
Attorney, Agent, or Firm—A. Robert Theibault

[57] ABSTRACT

The present disclosure is directed to a spring loaded cervical traction collar having front and rear discrete body halves in which each body half is split in half horizontally to define upper and lower front parts and upper and lower rear parts. A plurality of traction spring units each having double ended plunger rods having a head on each free end, a pair of closed ended cylinders and a spring is located in each of the cylinders. The springs are between the heads and the closed ends of the cylinders. Each cylinder is secured in one of said body halves. The springs urge the vertically opposed body halves in which each traction spring unit is secured to provide traction and are circumferentially spaced about the front and rear body halves and secured thereto with the axes of their plunger rods being substantially parallel to one another. Mating Velcro straps connect the upper front body part to the lower front body part while additional mating Velcro straps connect the upper rear body part to the lower rear body part and the spring loading of each unit permits selection of variable thrust loading circumferentially about the neck of a patient to provide prescribed vertical traction thrust of the head of a patient.

5 Claims, 2 Drawing Sheets

SPRING LOADED CERVICAL COLLAR

The present invention is directed to a spring loaded Cervical Collar which is light weight, easy to install and made of two mating halves which may be made of variably selected coil springs of varying load characteristics depending upon the patients condition and the degree of rigidity necessary for orthopedic constraint of the patients head and neck area.

The two piece collar which is removably placed about the patient's neck is of a semi-rigid light weight closed cell polyethylene or plastic construction somewhat similar to the Cervical Collar shown in U.S. Pat. No. 3,756,226, except that each section of my collar is horizontally split and variably spring loaded to apply the vertical pressure circumferentially about the neck in the direction from the shoulders toward the chin as necessary to immobilize the neck area to be treated by providing the vertically split collar with coil springs which permits movement of neck muscles, bone and tissue to the degree permitted by spring selection between the two collar halves and the therapy plan of the attending physician who as treatment progresses may wish to replace springs in the upper or lower half of the collar with stronger or weaker springs depending upon the progress of healing of the neck muscles, bone and tissue.

BACKGROUND ART

Prior to filling this application the most pertinent prior art known to me was:

L. T. McBEE, U.S. Pat. No. 2,474,200;
A. R. MOORE, U.S. Pat. No. 2,801,630;
A. TEUFEL, U.S. Pat. No. 2,807,260;
N. J. HALL, U.S. Pat. No. 2,820,455;
A. CALABRESE, et al, U.S. Pat. No. 3,756,226.

SUMMARY OF THE INVENTION

The present invention is directed to a light weight Spring Loaded Orthopedic Cervical Collar of the two piece, front and rear type each piece being split horizontally and separated vertically by compression spring units. The spring loading of which may be varied circumferentially about the neck of the patient, either partially around or completely around the neck as prescribed. Spring loading as well as spring placement may be varied per direction of physician, to control traction of the neck area. Springs of varying compression rates may be selected for placement into the spring units. Threaded caps on the free ends of the spring units will permit exchange of springs of one value for a spring of a weaker or stronger value.

The Spring Loaded Cervical Collar of the present invention is particularly useful in the neck area—post surgery, or for neck extension (traction) prior to surgery. It also has application in post whip lash cases, as well as for pinched nerves in the neck area.

The collar of the present invention is particularly useful after a neck fracture for applying the requisite tension to promote healing and/or possibly reducing a malaligned cervical spine.

BRIEF DESCRIPTION OF FIGURES OF DRAWINGS

BEST MODE FOR CARRYING OUT THE INVENTION

Figure 2:
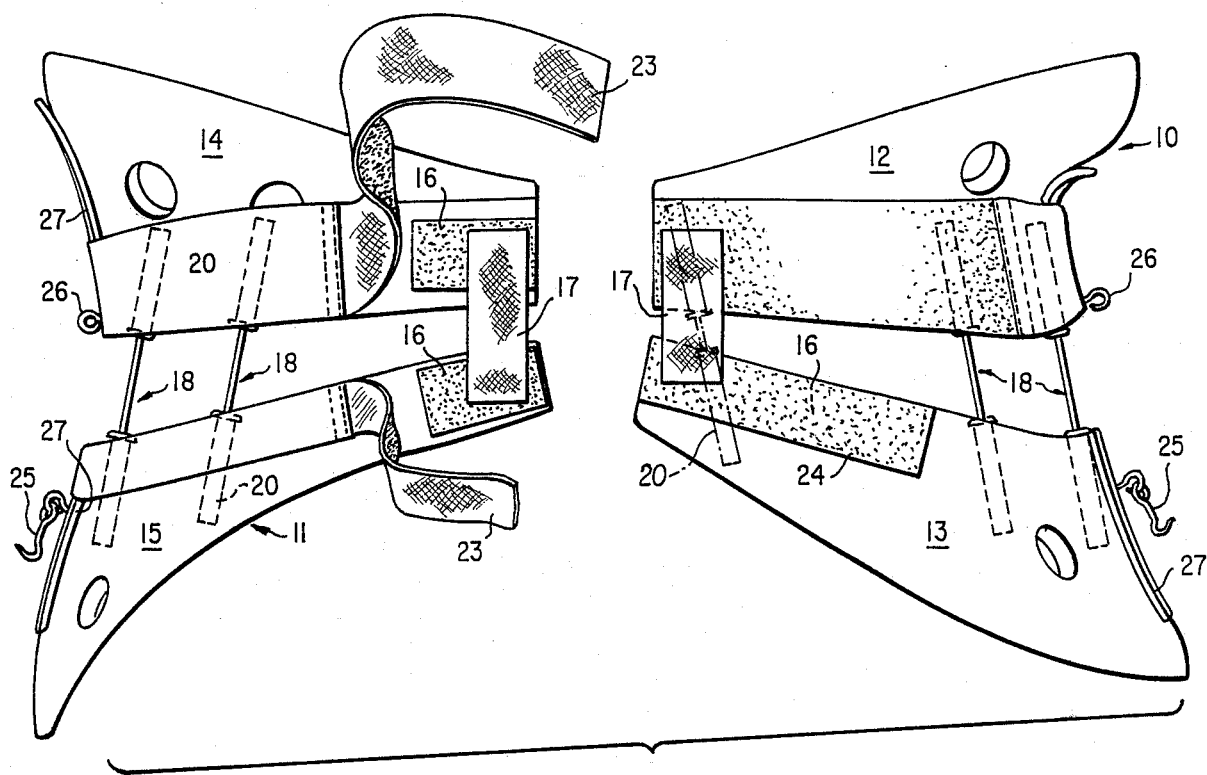
FIG. 2, is a side elevational view of the front and rear halves of my Cervical Collar of FIG. 1, with the upper and lower half of each collar in its fully extended condition.
Figure 1:
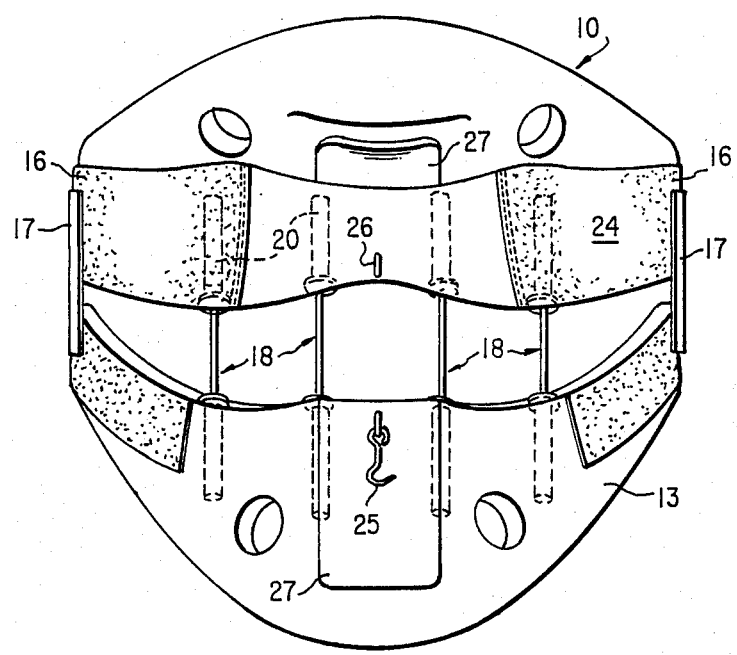
FIG. 1, is a front elevational view of my Spring Loaded Cervical Collar in its fully extended spring condition.
Figure 3:
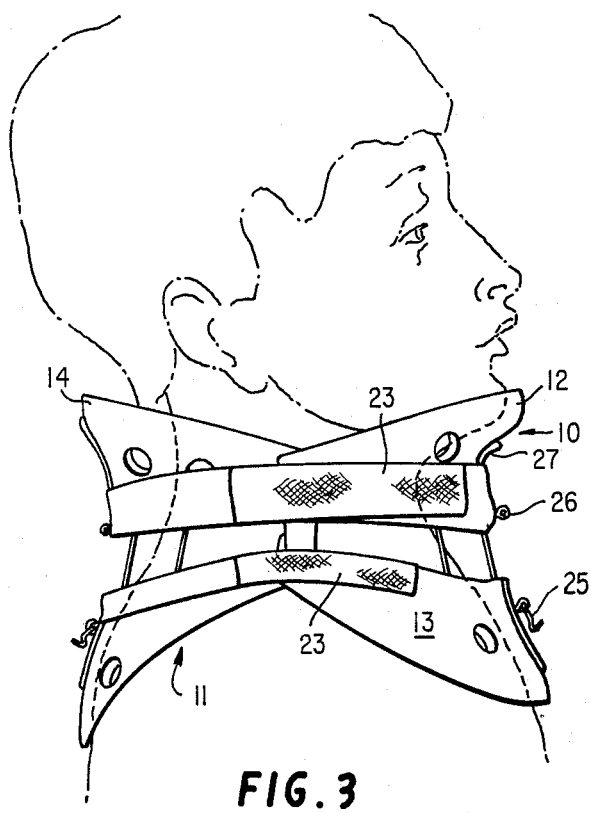
FIG. 3, is a side elevational view of my two half Spring Loaded Cervical Collar shown in its extended installed condition upon the outline of a patient.

Referring now to the drawings and for the moment to FIGS. 1 through 3, the Cervical Collar of the present invention comprises a first or front body half 10 and a second or rear body half 11, each of closed cell foam or semi-rigid plastic each of which is split into an upper portion 12 and a lower portion 13 and the second or rear body half 11, is likewise split into an upper portion 14 and a lower portion 15. As best seen in FIGS. 1 and 2, the upper and lower portions 12 and 13 are joined at the terminus of each side by mating Velcro tapes 16 and 17 or telescoping rods.

Figure 5:
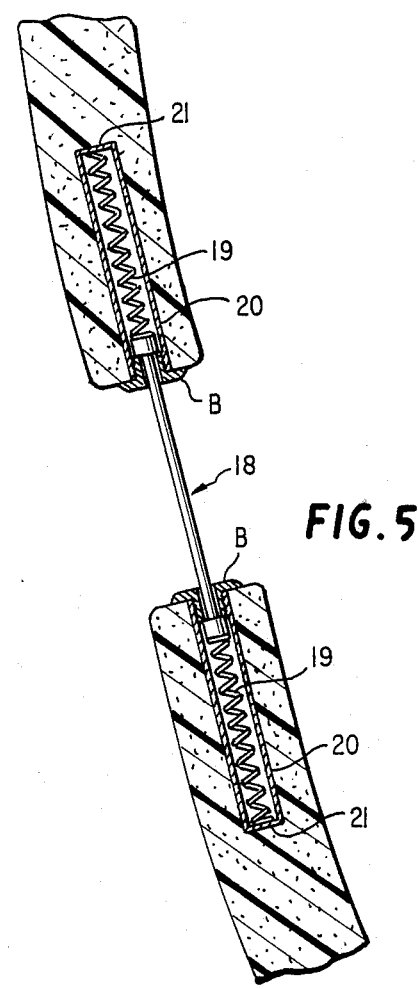
FIG. 5, is a vertical sectional view of the front part of the collar of FIG. 2, taken at an enlarged scale with the upper and lower half of the front collar with one of the spring assemblies in its fully expanded condition.

As best seen in FIGS. 1 and 2 the upper portion 14 is urged upwardly from the lower portion 15 by compression spring units 18 which are uniformly spaced at least partially about the circumference of the two collar halves. Each compression spring unit 18 has an internal compression spring 19 which may be either of flat wound or cylindrical cross-section compression spring wire. Each compression spring 19 is housed in a cylinder 20 having a closing end 21, which may be secured in place by a screw type boss B to assure that the head 21 of piston shaft 22 bears against the free end of the compression springs 19 housed in each cylinder 20 and is movable therewith as best seen in FIG. 5 and which permits the spring to be changed for one stronger or weaker.

The attending physician prescribing the Cervical Collar of the present invention may select springs of varying strength to cause the collar to impart the prescribed amount of traction in the neck circumferential area where needed. The spring units 19 may extend around the entire neck area or only partially about the neck at the discretion of the attending physician.

The two body halves of the collar 10 and 11 are retained in place about the neck of the patient by well known complemental Velcro fastening straps 23, 24 similar to those shown in FIG. 1 hereof or in U.S. Pat. No. 3,756,226.

The spring units may be cemented in place in drilled or molded openings in the foam structure upper and lower portions 12, 13, 14 and 15.

Figure 4:
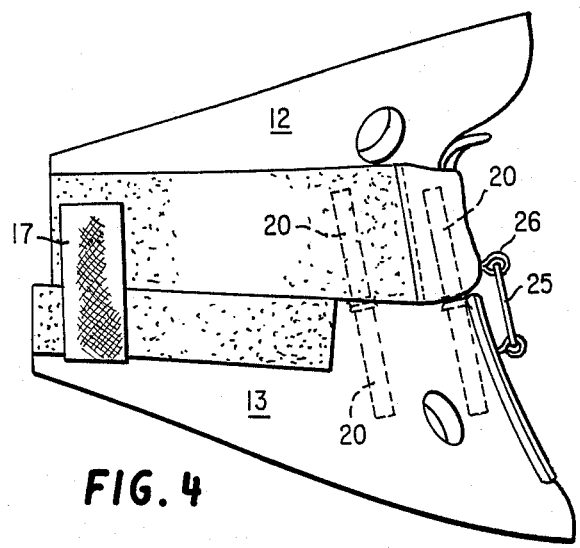
FIG. 4, is a side elevational view of the front half of the collar of FIG. 3 shown in its vertically compressed transport condition.
Figure 7:
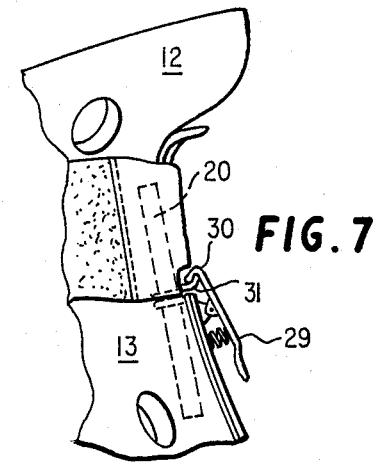
FIG. 7, is a fragmentary sectional view of one form of push button latch which may be employed in lieu of hooks and eyes to retain spring loaded upper and lower halves in the vertically loaded compressed transport condition.
Figure 6:
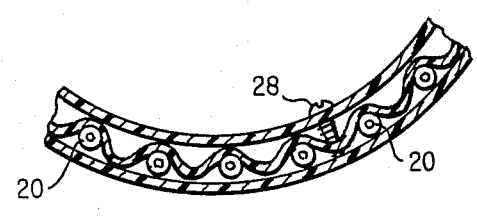
FIG. 6, is a fragmentary sectional view of the collar of the present invention having corrugated construction to promote light-weight structure to permit the use of a multiplicity of spring units.

The upper portion 12 and the lower portion 13 are retained in their compressed condition shown in FIG. 4 by a hook and eye arrangement 25, 26, or latching means shown in FIG. 7, for transportation in a compact condition. Member 27 is a reinforcing rigid support member, there being one on the front half 10 and one on the rear half 11.

As best seen in FIG. 7, the hook and eye retainer of FIG. 4 may be replaced with a spring loaded latch 29 which biases the hook 30 of the latch into engagement with the hook 31 to maintain the upper portion 12 into engagement with the lower portion 13.

What I claim is:

1. A spring loaded cervical traction collar comprising front and rear discrete body halves, each body half being split in half horizontally to define upper and lower front parts and upper and lower rear parts, a plurality of traction spring units each comprising a double ended plunger rod having heads on each free end, a pair of closed ended cylinders, a spring in each of said cylinders, each of said heads being located in one of said cylinders, said springs being between said heads and the closed ends of said cylinders, said cylinders each being secured in one of said body halves, said springs urging the vertically opposed body halves in which each traction spring unit is secured to provide traction, said traction spring units being circumferentially spaced about the front and rear body halves and secured thereto with the axes of their plunger rods being substantially parallel to one another, mating velcro straps connecting the upper front body part to the lower front body part, mating velcro straps connecting the upper read body part to the lower rear body part and the spring loading of each unit permitting selection of variable thrust loading circumferentially about the neck of a patient to provide prescribed vertical traction thrust of the head of a patient.

2. A spring loaded cervical collar as claimed in claim 1, further comprising retaining means connected between the upper and lower front and rear parts of each of said discrete body halves, said retaining means including one element secured to the upper part and another element secured to the lower part, said two elements being connectable together to compress the collar for transport.

3. A Cervical Collar as claimed in claim 1, wherein the springs are coils of flat wound helicies constructed within said closed ended cylinders.

4. A Cervical Collar as claimed in claim 2 wherein said retaining means is a hook and eye.

5. A Cervical Collar as claimed in claim 2 wherein said retaining means is a spring loaded latch.

* * * * *